| United States Patent [19] | [11] | 4,083,880 |
|---|---|---|
| Kagan et al. | [45] | Apr. 11, 1978 |

[54] PROCESS FOR PRODUCING $C_3$—$C_{20}$ ALIPHATIC ALCOHOLS

[76] Inventors: July Borisovich Kagan, ulitsa Alexeya Tolstogo, 26, kv. 27; Sergei Minovich Loktev, ulitsa Garibaldi, 21, korpus 3, kv. 55, both of Moscow; Gennady Alexeevich Nizov, ulitsa Kosmonavtov, 17-a, kv. 12, Novomoskovsk Tulskoi oblasti; Vyacheslav Alexandrovich Zhilin, ulitsa Mira, 8, kv. 27, Novomoskovsk Tulskoi oblasti; Alexandr Andreevich Zuev, ulitsa Kirova, 2/14, kv. 45, Novomoskovsk Tulskoi oblasti; Andrei Nikolaevich Bashkirov, ulitsa Novopeschanaya, 21, korpus 1, kv. 12, Moscow, all of U.S.S.R.

[21] Appl. No.: 798,001

[22] Filed: May 18, 1977

[51] Int. Cl.² ............................................. C07C 29/00
[52] U.S. Cl. .......................... 260/632 R; 252/455 R; 260/643 B
[58] Field of Search ..................... 260/632 R, 632 CA

[56] References Cited

U.S. PATENT DOCUMENTS

| 1,894,792 | 1/1933 | Schlecht et al. ................. 260/632 R |
| 2,739,169 | 3/1956 | Hagemeyer ................... 260/632 CA |
| 3,689,575 | 9/1972 | Tarhan ............................. 260/632 R |
| 3,733,362 | 5/1973 | Biale .............................. 260/632 CA |
| 3,933,919 | 1/1976 | Wilkinson ..................... 260/632 CA |

*Primary Examiner*—Joseph E. Evans
*Attorney, Agent, or Firm*—Lackenbach, Lilling & Siegel

[57] ABSTRACT

A process for producing $C_3$-$C_{20}$ aliphatic alcohols which comprises reacting carbon monoxide, hydrogen and acetylene, on a fused iron catalyst, in the form of a solution in a liquid medium inert to said reagents and said iron catalyst being present in this medium.

As the liquid medium use is made of a fraction of aliphatic saturated $C_{10}$-$C_{18}$ alcohols or a fraction of $C_{12}$-$C_{20}$ paraffin hydrocarbons, or a mixture thereof. The synthesis is conducted at a temperature ranging from 170° to 220° C under a pressure of from 20 to 200 atm.

The process according to the present invention makes it possible to increase concentration of acetylene in the reaction medium, whereby the catalyst space-time yield is increased. Moreover, the present invention enables a longer stable service life of the catalyst owing to the isothermal character of the catalyst bed and higher thermal stability of the process.

6 Claims, No Drawings

PROCESS FOR PRODUCING $C_3$—$C_{20}$ ALIPHATIC ALCOHOLS

The present invention relates to the art of organic synthesis and, more specifically, to processes for producing $C_3$-$C_{20}$ aliphatic alcohols which are useful commercially mainly as the starting stock for the preparation of plasticizers, surfactants and detergents, additives to oils and fuels.

Known in the art is a process for producing higher aliphatic alcohols by way of a gas-phase synthesis from carbon monoxide, hydrogen, and acetylene on a stationary bed of a fused iron catalyst under a pressure within the range of from 50 to 200 atm at a temperature of from 170° to 210° C under a partial pressure of acetylene of up to 1.5 atm.abs.

This prior art process has a disadvantage residing in a relatively low space-time yield of the catalyst (60–65 kg/m³ per hour), which is caused by the difficulty of maintaining constant temperature over the height and cross-section of the catalyst bed, taking into account a high thermal effect of the reaction. The process does not enable an increase of acetylene concentration within the reaction zone due to the prohibition prescribed by safety norms to operate under a partial pressure of acetylene above 1.5 atm.abs. with the total gas pressure being of any value. For this reason, in the above-mentioned process the maximum tolerable concentration of acetylene in the gas mixture is 3% by volume under a pressure of 50 atm, 1.5% by volume under a pressure of 100 atm, and 0.75% by volume under a pressure of 200 atm.

Efforts to increase the catalyst productivity in the gas-phase synthesis by increasing the temperature or space velocity of the gas mixture resulted in greater overheating in the catalyst zone, impaired process selectivity, and accelerated deactivation of the catalyst.

It is an object of the present invention to provide a high-productivity process for producing higher aliphatic alcohols from carbon monoxide, hydrogen and acetylene.

The present invention is directed to the provision of novel technological steps in the synthesis of higher aliphatic alcohols from carbon monoxide, hydrogen and acetylene enabling a higher concentration of acetylene in the reaction mixture and, hence, an increased yield of the product while simultaneously ensuring isothermal character and thermal stability of the process.

This object is accomplished by a process for producing $C_3$-$C_{20}$ aliphatic alcohols by the synthesis thereof from carbon monoxide, hydrogen, and acetylene in the presence of a fuxed iron catalyst at elevated temperatures and pressures, wherein in accordance with the present invention carbon monoxide, hydrogen and acetylene and brought into reaction while being dissolved in a liquid medium comprising a fraction of saturated aliphatic $C_{10}$-$C_{18}$ alcohols, or a fraction of paraffin $C_{12}$-$C_{20}$ hydrocarbons, or a mixture of said fraction of saturated alcohols and said fraction of paraffin hydrocarbons; the reaction is conducted on a catalyst containing 92 to 95% by weight of $Fe_3O_4$, 0.5 to 2% by weight of an alkaline promoter such as $K_2O$ or $Na_2O$, and 3 to 7.5% by weight of structure promoters such as $V_2O_5$, $Al_2O_3$, $SiO_2$, under a pressure of from 20 to 200 atm and at a temperature ranging from 170 to 220° C.

In accordance with the present invention, said liquid medium may contain 10 to 50% by weight of N-methylpyrrolidone which facilitates dissolution of acetylene.

Two embodiments of the synthesis of higher aliphatic alcohols from carbon monoxide, hydrogen, and acetylene are possible, depending on the mode of dissolving thereof in a liquid medium; nevertheless, in both embodiments the liquid medium should completely cover the catalyst, i.e. the catalyst should be submerged in said liquid medium.

The liquid medium must have a definite combination of physico-chemical properties, namely, it must be capable of dissolving acetylene, carbon monoxide and hydrogen, be inert towards said reagents and the iron catalyst, and be stable to chemical transformations under the synthesis condition.

A first embodiment which is a preferable one comprises preliminary dissolving of the starting gaseous components in said liquid medium outside the catalysis zone.

Such a liquid medium containing the starting reagents in the dissolved form, i.e. a solution of the starting reagents, is continuously passed at a space velocity of from 500 to 10,000 hr$^{-1}$ through the catalyst bed. In this case the highest degree of saturation of the liquid medium with the reagents is ensured along with the absence of the gaseous reagents in the catalysis zone. Therewith, concentration of acetylene in the reaction mixture can be increased as compared to its initial concentration in the starting gaseous mixture.

A second embodiment resides in that the starting gaseous reagents are dissolved in the liquid medium passed through the catalyst bed directly in the zone of the catalyst location.

In both embodiments pressure in the catalyst zone is maintained within the range of from 20 to 200 atm, preferably from 50 to 150 atm; temperature is maintained within the range of from 170° to 220° C, preferably from 190° to 200° C. Under these conditions, synthesis of higher aliphatic alcohols proceeds on the catalyst according to the following general scheme: $CH{\equiv}CH + nCO + (2n + 1)H_2 \rightarrow C_{n+2}H_{2n+5}OH + (n-1) H_2O$, wherein $n$ is within the range of from 1 to 18.

As the iron catalyst use is made of a fuxed iron catalyst containing 92 to 95% by weight of $Fe_3O_4$, 0.5 to 2% by weight of an alkaline promoter, i.e. $K_2O$ or $Na_2O$ and 3 to 7.5% by weight of structural promoters, in the present case these being oxides non-reducible at temperatures within the range of from 300 to 500° C, i.e. $V_2O_5$, $Al_2O_3$, $SiO_2$. The structure promotors are contained in the catalyst in the following amounts: 0.5 to 1.5% by weight of $V_2O_5$, 2,2 to 5.3% by weight of $Al_2O_3$, and 0.3 to 0.7% by weight of $SiO_2$.

The process according to the present invention makes it possible:

(1) To increase acetylene concentration in the reaction mixture, thus increasing the reaction rate and, hence, the process space-time yield.

(2) To maintain a constant temperature over the height and cross-section of the catalyst bed, thus retaining the catalyst selectivity with an increase in the speed of the synthesis reaction.

(3) To eliminate accumulation on the catalyst of high-melting synthesis products blocking the catalyst surface and, hence, lowering its activity.

(4) To enhance the thermal stability of the process and reliability of the reactor operation owing to the presence of a moving liquid medium which presents disturbances in the heat conditions of the catalyst bed.

(5) To extend the period of stable operation of the catalyst.

(6) To achieve high space-time yield of the catalyst within the range of from 400 to 750 kg/m$^3$ of the catalyst per hour.

These and other advantages of the present invention will become more fully apparent from the following detailed description of the process and corresponding examples.

The iron catalyst employed in the synthesis according to the present invention is prepared using conventional procedures, namely by way of oxidative fusion of metallic iron or electric fusion of black iron oxide with the addition of promoters, i.e. 0.5 to 2% by weight of $K_2O$ or $Na_2O$, 0.5 to 1.5% by weight of $V_2O_5$, 2.2 to 5.3% by weight of $Al_2O_3$, and 0.3 to 0.7% by weight of $SiO_2$. After cooling, the fused cake is crushed and a fraction of a required particle size is collected, for example a fraction with a particle size of from 2 to 3 or 3 to 5 mm. The selected fraction is then subjected to reduction with hydrogen using conventional methods, i.e. under pressures of from 1 to 50 atm and at a temperature within the range of from 400 to 500° C to convert iron oxides completely to metallic iron.

The reduced catalyst is placed into a reactor adapted for the syntehsis. During operation the catalyst should be submerged in the liquid medium of the above-mentioned composition. The reactor may be of various designs, such as of a tubular type; however, in all cases it should ensure vigorous stirring or circulation of the liquid medium being passed through the catalyst bed.

The starting gaseous reagents, i.e. carbon monoxide, hydrogen, and acetylene should be dissolved in the liquid medium. This is ensured by dissolving the starting gaseous reagents in the liquid medium directly in the catalyst location zone or, preferably, somewhere on the way of the liquid medium towards said zone.

As the starting gases use is made of acetylene-containing mixtures of carbon monoxide and hydrogen which may contain 0.5 to 10% by volume of acetylene, 65 to 20% by volume of carbon monoxide, 30 to 60% by volume of hydrogen; the balance being inert components (4.5 to 10% by volume), i.e. nitrogen, carbon dioxide, methane. To ensure a required pressure and safe concentration of acetylene these gases are added with mixtures of carbon monoxide and hydrogen containing 30 to 60% by volume of CO and 40 to 70% by volume of $H_2$. Such gases are commercially available or may be prepared by mixing the starting components.

As the starting gases use can be made of industrial gaseous mixtures, such as a reaction gas from industrial oxidative pyrolysis of methane of acetylene, or an off-gas from this process after washing-out substantially the total amount of acetylene therefrom. Typical averaged compositions of such gases are given in the following Table (percent by volume).

| Gas type | CO | $H_2$ | $C_2H_2$ | $CH_4$ | $CO_2 + N_2$ |
|---|---|---|---|---|---|
| Reaction gas from methane pyrolysis | 27 | 54 | 7 | 7 | the balance |
| Off-gas from methane pyrolysis | 30 | 56 | 0.5 | 8 | the balance |

As the liquid medium for the synthesis according to the present invention use is made, as has been mentioned hereinbefore, of fractions of saturated $C_{10}$-$C_{18}$ aliphatic alcohols, or fractions of paraffin $C_{12}$-$C_{20}$ hydrocarbons, or a mixture thereof. Boiling temperature of said fractions of alcohols and hydrocarbons is higher than the working temperature of the synthesis, i.e. above 200°-220° C. Said fractions of aliphatic alcohols and paraffin hydrocarbons are commercially available. Solubility of the reagents at 42° and 60 atm is (Ncm$^3$/cm$^3$ of the liquid medium): in $C_{10}$-$C_{18}$ alcohols; 6.0 for CO, 3.0 for $H_2$; in $C_{12}$-$C_{20}$ paraffins: 5.5 for CO and 3.6 for $H_2$. Solubility of acetylene at 42° C under total pressure of 60 atm and partial pressure of 0.62 atm.abs. is 1.0 in $C_{10}$-$C_{18}$ alcohols and 1.2 in $C_{12}$-$C_{20}$ paraffins.

To adjust solubility of the starting components, in particular to increase solubility of acetylene, said fractions are added, as has been mentioned hereinbefore, with N-methylpyrrolidone (b.p. 206° C) in an amount ranging from 10 to 50% by weight of the total liquid medium.

The process according to the present invention can be performed in two embodiments depending on the selected mode of dissolution of the starting gaseous reagents in the liquid medium.

The most preferable embodiment of the synthesis according to the present invention contemplates dissolution of the gaseous reagents in the liquid medium preliminarily and outside the catalyst location zone. In this case, solution of the reagents is fed into the catalyst at a rate of from 500 to 10,000 volumes of the solution per volume of the catalyst (hereinafter is designated as hr$^{-1}$).

The second embodiment of the synthesis according to the present invention stipulates dissolution of the starting gaseous reagents in the same zone, wherein the catalyst submerged into the liquid medium is located. This means that gaseous reagents are fed into the same volume of the reactor, wherein the catalyst bed submerged into the liquid medium is located and, hence, dissolution thereof occurs in the same volume, wherein the catalyst is placed, i.e. in the catalysis zone.

In both embodiments pressure in the catalysis zone is maintained within the range of from 20 to 200 atm, preferably from 50 to 150 atm; temperature is varied within the range of from 170° to 220° C, preferably from 190° to 200° C.

At temperatures below 170° C and under pressures below 20 atm the reaction of synthesis is retarded so that it even becomes useless. With temperatures exceeding 220° C and pressures over 200 atm the reaction of carbon monoxide and hydrogen without any participation of acetylene starts to play a growing role, whereby the process selectivity is impaired.

The heat evolved during the reaction is consumed for heating and evaporation of the liquid medium components as well as for heating of the reactor walls, wherethrough this heat is dissipated into the environment.

The liquid medium discharged from the catalysis zone is enriched with the synthesis products which are then separated by conventional methods such as purging or stripping. Thereafter, the synthesis products are condensed, separated and withdrawn from the system. After separation of the substantial portion of the synthesis products, the liquid medium is delivered to a zone of saturation with the starting gaseous reagents, or is fed directly into the catalysis zone.

The high-boiling products partly remaining in the liquid medium gradually increase volume of the latter.

To maintain the constant volume, a portion of the liquid medium is periodically discharged from the system.

The process according to the present invention makes it possible to obtain a mixture of higher aliphatic primary alcohols, predominantly of a normal structure, with minor amounts of unsaturated alcohols, carbonyl compounds and esters. To purify the resulting product, said impurities are converted to saturated alcohols. To this end, the resulting mixture of higher aliphatic alcohols is subjected to selective catalytic hydrogenation by means of hydrogen using conventional methods such as hydrogenation on a copper-chromium or a nickel-chromium catalyst. The mixture of saturated alcohols obtained from such hydrogenation is separated into appropriate fractions according to final applications thereof. Thus, for the preparation of phthalate plasticizing agents, fractions $C_5$-$C_7$, $C_7$-$C_9$, $C_6$-$C_8$ and the like are recovered while for the production of surfactants such as alkylsulphates or ethoxylates fractions $C_{12}$-$C_{18}$, $C_{10}$-$C_{16}$, $C_{12}$-$C_{16}$ and the like are recovered.

For a better understanding of the present invention some specific examples illustrating the synthesis are given hereinbelow.

EXAMPLE 1

An iron catalyst having the following composition, percent by weight: 95 $Fe_3O_4$, 0.5 $K_2O$, 4.5 of structure promoters (1.5 $V_2O_5$, 2.3 $Al_2O_3$, 0.7 $SiO_2$) is prepared by conventional techniques of oxidative fusion or electric fusion. After crushing the cooled fused material, particles with a size of 2-3 mm are screened; these are then reduced by a hydrogen-containing gas such as hydrogen or a hydrogen-nitrogen mixture at a temperature of from 430° to 450° C under a pressure of 20 to 50 atm for a period of time ensuring substantially total reduction of iron oxides to metallic iron. This takes, under the above-mentioned conditions, about 10 to 12 hours. The degree of reduction completeness is determined by discontinuation of water liberation.

Into a tubular reactor there are placed 30 ml of the reduced catalyst particles with a size of 2-3 mm. Through the catalyst bed a liquid medium is pumped upwards containing dissolved therein carbon monoxide, hydrogen, and acetylene. As the liquid medium a fraction of primary $C_{10}$-$C_{18}$ alcohols is used (boiling range is 220° to 360° C under 760 mm Hg). Dissolution of the components of the starting gas having the composition: 44 vol.% of carbon monoxide, 53 vol. % of hydrogen, and 1.2 vol.% of acetylene, the balance being constituted by $CH_4$, $CO_2$, $N_2$, is conducted, while bubbling the gas through said liquid medium prior to admission of the latter into the catalysis zone. The concentration of acetylene in the reaction mixture is 2 times as high as that in the starting gas employed under the synthesis conditions.

The synthesis conditions are: pressure 100 atm, temperature 190° C; supply rate of the liquid medium is 1000 volumes of the liquid medium per volume of the catalyst per hour. Temperature in the catalyst zone is measured by means of thermocouples to detect constant temperatures over the height and cross-section of the catalyst bed (temperature variations did not exceed ± 1° C).

The catalyst has shown stability of operation for more than 500 hours, which is due to stable thermal conditions and removal of high-melting products from the catalyst surface.

Recovering the synthesis products from the liquid medium discharged from the reactor is effected by means of purging or stripping. The recovered synthesis products are condensed separated and withdrawn from the system. After recovering the synthesis products, the liquid medium is delivered to the stage of enrichment with the starting gaseous products, whereafter it is recycled to the reactor for the synthesis.

Space-time yield of the catalyst relative to the desired product is 400 kg/m³ of the catalyst per hour, which is 6 times higher than the space-time yield of the prior art gas-phase process.

The thus-produced mixture of higher aliphatic alcohols containing impurities of other oxygen-containing compounds is subjected to hydrogenation (to convert the above-mentioned impurities to alcohols) by a conventional method over a copper-chromium catalyst under a pressure of hydrogen within the range of from 100 to 200 atm, at a temperature of from 230° to 250° C, at an hourly space velocity of the liquid stock of 1-2 hr$^{-1}$ and that of hydrogen of 2,000 to 5,000 hr$^{-1}$. The resulting hydrogenate is separated to fractions of alcohols by rectification. The yield of alcohol fractions as distilled is, percent by weight of the total amount of the alcohols, as follows: 9% of $C_1$-$C_3$ fraction; 7% of $C_4$ fraction, 32% of $C_5$-$C_7$ fraction, 31% of $C_8$-$C_{12}$ fraction, 21% of $C_{13}$-$C_{18}$ fraction.

EXAMPLE 2

The catalyst is prepared, reduced and placed into a tubular reactor in a manner similar to that described in the foregoing Example 1. Charged into the reactor is a liquid medium having the same composition as in Example 1. Directly under the catalyst bed completely submerged into the liquid medium the starting gas is fed having the following composition: 42% by volume of carbon monoxide, 56% by volume of hydrogen, 1% by volume of acetylene; the balance being constituted by nitrogen, carbon dioxide, methane. The synthesis conditions are: pressure 100 atm, temperature 190° C, hourly space velocity of the gas fed into the reactor is 15,000 hr$^{-1}$. Dissolution of the gas components in the liquid medium is effected within the same volume wherein the catalyst is placed; the non-dissolved portion of the gas is passed through the catalyst bed in the upward direction thus intermixing the medium and entraining the resulting products of the synthesis. Therefore, in the reaction volume the starting components are present in both dissolved and non-dissolved state. Circulation of the liquid medium through the catalyst bed is effected due to the difference in density values of the liquid medium and the gas (the principle of a pneumatic lift or air-lift).

Separation of the synthesis products and hydrogenation thereof is conducted as described in the foregoing Example 1. The catalyst space-time yeild is 280 kg/m³ of the catalyst per hour. The yield of fractions of alcohols is; percent by weight: $C_1$-$C_3$ 12%, $C_4$ - 8%, $C_5$-$C_7$ - 31%, $C_8$-$C_{12}$ - 29%, $C_{13}$-$C_{18}$ - 20%.

EXAMPLE 3

The catalyst is prepared, reduced and placed into a tubular reactor according to the procedure described in Example 1 hereinbefore. As the liquid medium use is made of a fraction of $C_{12}$-$C_{20}$ paraffin hydrocarbons (boiling range is of from 210° to 350° C under 760 mm Hg). During the synthesis the liquid medium is enriched with aliphatic alcohols resulting from the synthesis and, consequently, comprises a mixture of aliphatic alcohols and paraffin hydrocarbons.

The synthesis is conducted under the pressure of 100 atm and at the temperature of 190° C. The starting gas has the following composition, percent by volume: 40% of carbon monoxide, 58% of hydrogen, 1.1% of acetylene, the balance being represented by nitrogen and carbon dioxide. Separation of the products and hydrogenation thereof is conducted in accordance with the procedure described in Example 1 hereinbefore.

The catalyst space-time yield is 370 kg/m$^3$ of the catalyst per hour.

After 500 hours of non-stop operation the catalyst has practically retained its initial activity which is mainly due to a continuous extraction, from the catalyst, of high-melting synthesis products. The yield of fractions of alcohols is the following, percent by weight: 10% of the fraction $C_1$-$C_3$, 7% of the $C_4$ fraction; 30% of the $C_5$-$C_7$ fraction; 31% of the $C_8$-$C_{12}$ fraction and 22% of the $C_{13}$-$C_{18}$ fraction.

EXAMPLE 4

The catalyst is prepared, reduced and placed into a tubular reactor according to the procedure described in the foregoing Example 1. The synthesis, recovery of the products and hydrogenation thereof are conducted as described in Example 1 hereinbefore.

As the liquid medium use is made of a mixture consisting of 50% by weight of aliphatic $C_{10}$-$C_{18}$ and 50% by weight of paraffin hydrocarbons $C_{12}$-$C_{20}$. The catalyst space-time yield is 390 kg/m$^3$ of the catalyst per hour. The product boiling-range distribution is similar to that described in Example hereinbefore.

EXAMPLE 5

The catalyst is prepared, reduced and placed into a tubular reactor as described in Example 2 hereinbefore. The synthesis, recovery of the products and hydrogenation thereof are conducted as described in Example 1 hereinbefore.

As the liquid medium use is made of a mixture containing 50% by weight of paraffin $C_{12}$-$C_{20}$ hydrocarbons and 50% by weight of N-methylpyrrolidone. The synthesis is conducted under the pressure of 100 atm using a starting gas containing the following components, percent by volume: 40% of carbon monoxide, 1% of acetylene, 54% of hydrogen, the balance being represented by nitrogen and carbon dioxide.

The synthesis duration is 196 hours. The catalyst space-time yield is 240 kg/m$^3$ of the catalyst per hour at the temperature of 180° C and 350 kg/m$^3$ of the catalyst per hour at the temperature 190° C. The product boiling-range distribution is similar to that described in Example 1 hereinabove.

EXAMPLE 6

The catalyst is prepared, reduced and placed into a tubular reactor as described in Example 1, and the synthesis is conducted as in described Example 2 hereinbefore.

As the liquid medium use is made of a mixture containing 65% by weight of a fraction of aliphatic $C_{10}$-$C_{18}$ alcohols and 35% by weight of N-methylpyrrolidone. The catalyst spacetime yield is 340 kg/m$^3$ of the catalyst per hour. The product is boiling-range distribution similar to that described in Example 2 hereinbefore.

EXAMPLE 7

The catalyst is prepared by following the procedure described in Example 1 hereinbefore; it is added with 2% by weight of $K_2O$. The resulting catalyst is reduced and placed into a tubular reactor as described in Example 1. The synthesis is conducted as in Example 1; except that the pressure is 50 atm and temperature is 190° C. The catalyst space-time yield is 660 kg/m$^3$ of the catalyst per hour. The products is boiling-range distribution is similar to that described in Example 1.

EXAMPLE 8

An iron catalyst containing 1.5% by weight of $K_2O$ is reduced as described in Example 1 hereinbefore. The synthesis products are separated as in Example 1. Into a tubular reactor there is charged 0.2 liter of the catalyst particles with a size of 3 to 5 mm.

As the liquid medium use is made of a fraction of $C_{12}$-$C_{18}$ aliphatic hydrocarbons which is treated with a gas having the following composition, percent by volume: 33% of carbon monoxide, 58% of hydrogen, 3.0% of acetylene, the balance being nitrogen, carbon dioxide, methane. In this case the concentration of acetylene in the liquid medium is 4 times as high as in the starting gas mixture.

The liquid medium is pumped upwardly through the catalyst bed at the hourly space velocity of 9,000 volumes per 1 volume of the catalyst per hour. Pressure in the reactor is 50 atm and temperature is 200° C. The catalyst space-time yield is 700 to 750 kg/m$^3$ of the catalyst per hour, i.e. 11 times higher than the productivity of the gas-phase process. The product boiling-range distribution is similar to that of Example 1 hereinbefore.

EXAMPLE 9

The catalyst is prepared, reduced and placed into a reactor as described in Example 1. The synthesis is also conducted as in Example 1, except that the reaction pressure is 200 atm. The catalyst space-time yield is 520 kg/m$^3$ of the catalyst per hour. The yield of fractions of alcohols is the following, percent by weight: 7% of the $C_1$-$C_3$ fraction, 6% of the $C_4$ fraction, 29% of the $C_5$-$C_7$ fraction, 33% of the fraction $C_8$-$C_{12}$; 25% of the $C_{13}$-$C_{18}$ fraction.

EXAMPLE 10

The catalyst is prepared, reduced and placed into a reactor according to the procedure described in the foregoing Example 1. The synthesis is conducted as described in Example 1, except that the temperature employed is 220° C. The catalyst space-time yield is 500 kg of liquid products per 1 m$^3$ of the catalyst per hour, including 20% of hydrocarbons.

EXAMPLE 11

The catalyst is prepared, reduced and placed into a reactor as described in Example 1. The synthesis is conducted as described in Example 1, except that the liquid medium is supplied at the rate of 500 volumes per volume of the catalyst per hour. The catalyst space-time yield is 220 kg/m$^3$ of the catalyst per hour. The product boiling-range distribution is similar to that described in Example 1.

EXAMPLE 12

In the preparation of the catalyst by the procedure described in Example 1, the catalyst is added with 1% by weight of $Na_2O$ and 3% by weight of structural promoters including 0.5% by weight of $V_2O_5$, 2.2% by weight of $Al_2O_3$, 0.3% by weight of $SiO_2$. The resulting catalyst is reduced and placed into a tubular reactor as described in Example 1. The synthesis is conducted as in Example 1, except that as the liquid medium use is made of a fraction of $C_{12}$-$C_{20}$ paraffin hydrocarbons as in Example 3, and the process temperature is 180° C. The catalyst space-time yield is 250 kg/m³ of the catalyst per hour. The hydrogenated product boiling-range distribution is as follows, percent by weight: 8% of the fraction $C_1$-$C_3$, 6% of the fraction $C_4$, 30% of the fraction $C_5$-$C_7$; 32% of the fraction $C_8$-$C_{12}$ and 24% of the fraction $C_{13}$-$C_{18}$.

EXAMPLE 13

In the preparation of the catalyst by the procedure described in Example 1 hereinbefore, the catalyst is added with 2% by weight of $K_2O$ and 7.5% by weight of structural promoters, including 1.5% by weight of $V_2O_5$, 5.3% by weight of $Al_2O_3$, 0.7% by weight of $SiO_2$. The resulting catalyst is reduced and placed into a tubular reactor according to the procedure described in Example 1, except that the reaction pressure is 50 atm and temperature is 200° C. The catalyst space-time yield is 590 kg/m³ of the catalyst per hour. The product boiling-range distribution is similar to that of Example 1 hereinbefore.

What is claimed is:

1. A process for producing $C_3$-$C_{20}$ aliphatic alcohols by catalytically reacting carbon monoxide, hydrogen, and acetylene, all being dissolved in a liquid medium selected from the group consisting of a fraction of saturated aliphatic $C_{10}$-$C_{18}$ alcohols a fraction of paraffin $C_{12}$-$C_{20}$ hydrocarbons, and a mixture of both said fractions, said reagents being reacted on a catalyst containing 92 to 95% by weight of $Fe_3O_4$, 0.5 to 2% by weight of an alkaline promoter selected from the group consisting of $K_2O$ and $Na_2O$, 3 to 7.5% by weight of structural promoters selected from the group of metal oxides consisting of $V_2O_5$, $Al_2O_3$, $SiO_2$ at a temperature ranging from 170° to 220° C under a pressure of from 20 to 200 atm.

2. A process as claimed in claim 1, wherein said liquid medium contains 10 to 50% by weight of N-methylpyrrolidone.

3. A process as claimed in claim 1, wherein the synthesis is conducted under a pressure of from 50 to 150 atm and at a temperature within the range of from 190° to 200° C.

4. A process as claimed in claim 1, wherein dissolution of the gaseous reagents is performed in the liquid medium preliminarily outside the catalyst zone and the resulting solution is continuously passed through the catalyst bed at an hourly space velocity of from 500 to 10,000 $hr^{-1}$.

5. A process as claimed in claim 1, wherein dissolution of the starting gaseous reagents is performed in a moving liquid medium directly in the catalyst zone.

6. A process as claimed in claim 1, wherein the content of the structural promoters in the catalyst is: 0.5 to 1.5% by weight of $V_2O_5$, 2.2 to 5.3% by weight of $Al_2O_3$, 0.3 to 0.7% by weight of $SiO_2$.

* * * * *